United States Patent [19]

Croci et al.

[11] 4,182,709

[45] Jan. 8, 1980

[54] MANUFACTURE OF SEMI-SYNTHETIC PENICILLIN ANTIBIOTICS

[75] Inventors: Marco Croci, Milan; Gino Cotti, Monza, both of Italy

[73] Assignee: Glaxo Group Limited, London, England

[21] Appl. No.: 914,288

[22] Filed: Jun. 9, 1978

Related U.S. Application Data

[63] Continuation of Ser. No. 758,322, Jan. 10, 1977, abandoned.

[30] Foreign Application Priority Data

Jan. 15, 1976 [IT]  Italy ................................ 47642 A/76

[51] Int. Cl.² .......................................... C07D 499/68
[52] U.S. Cl. .................................................. 260/239.1
[58] Field of Search ...................................... 260/239.1

[56] References Cited

FOREIGN PATENT DOCUMENTS

| | | | |
|---|---|---|---|
| 959853 | 6/1964 | United Kingdom | 260/239.1 |
| 964449 | 7/1964 | United Kingdom | 260/239.1 |
| 1008468 | 10/1965 | United Kingdom | 260/239.1 |
| 1269697 | 4/1972 | United Kingdom | 260/239.1 |
| 1391838 | 4/1975 | United Kingdom | 260/239.1 |

*Primary Examiner*—Gerald A. Schwartz
*Attorney, Agent, or Firm*—Bacon & Thomas

[57] ABSTRACT

A process for preparing semi-synthetic penicillin antibiotics, especially ampicillin, is disclosed which comprises acylating a silylated 6-aminopenicillanic acid in the presence of primary or secondary carboxamide bases as hydrogen halide acceptors. The products may be obtained in good yield and high purity and the amount of toxic contaminants in the products is significantly reduced, thus substantially eliminating unpleasant side-effects.

10 Claims, No Drawings

MANUFACTURE OF SEMI-SYNTHETIC PENICILLIN ANTIBIOTICS

This is a continuation, of application Ser. No. 758,322, filed Jan. 10, 1977 now abandoned.

This invention relates to improvements in or relating to the manufacture of semi-synthetic penicillin antibiotics.

Numerous processes have been proposed for preparing the semi-synthetic range of penicillin antibiotics, and particularly ampicillin. These proposals have generally involved the acylation of 6-aminopenicillanic acid (6-APA) or a protected derivative thereof using, for example, an acid halide serving to introduce the desired acyl group. Particularly favoured protected derivatives have been those which may readily be cleaved in situ once the acylation has been effected.

One of the more favoured types of protected derivative of 6-APA has been the mono- or bis- silylated intermediate. Silylated intermediates have been widely used for many years since they have the advantages not only that the silyl groups assist in solubilising the penicillin compounds so that reaction may be performed in aprotic solvents, thus preventing a certain amount of $\beta$-lactam hydrolysis, but also that they may readily be cleaved in situ following acylation. British Pat. Nos. 959,853; 964,449 and 1,008,468 for example, describe both the preparation and subsequent use of silylated 6-APA intermediates in penicillin antibiotic production.

The actual acylation step using the silylated intermediate is frequently carried out using an acid halide of the carboxylic acid whose acyl group it is proposed to introduce in the presence of an organic base as hydrogen halide acceptor. The great majority of bases previously employed or proposed to be employed in this role have been amines, particularly secondary or tertiary amines such as trialkylamines, dialkylanilines, piperidines or pyridines. Furthermore such acylations have occasionally been proposed to be carried out in tertiary amide solvents, as in for example, British Pat. No. 959,853.

It has been a disadvantage of such known processes that the acylated antibiotic products obtained tend to be contaminated, even after purification, with minor amounts of the base or solvent employed in their preparation which are extremely difficult to remove from the antibiotic and which frequently possess significant toxicity. It is, of course, desirable that any pharmaceutical product be prepared and sold in the highest degree of purity possible and it is a fact that even the very small amounts of base with which the antibiotic product is contaminated may produce unpleasant side effects when the antibiotics are administered. These include headaches, nausea or drowsiness and it is accordingly highly important either that the amounts of such contaminants in the antibiotic be minimised, or that the contaminants possess lower toxicity.

The disadvantages outlined above have applied particularly to the dialkylanilines when these have been used as bases. The dialkylanilines, and especially dimethylaniline, have been extensively used commercially as hydrogen halide acceptors in the acylation reaction since their $pK_b$ values fall within the critical narrow range for the maximisation of yield of antibiotic product and avoidance of side-reactions. Unfortunately, they have been found to occlude to a small extent into the antibiotic product and they also possess marked toxicity. The small amounts of, for example, dimethylaniline which occlude into the antibiotic product are sufficient to produce unpleasant side-effects, including those outlined above.

We have now found that if acylation of the silylated 6-APA intermediate using an acid halide is carried out in the presence of a primary or secondary carboxamide base as hydrogen halide acceptor, the good yields of product which have previously been obtained by this type of acylation may be maintained, even on a commercial scale, and also, the antibiotic product obtained is significantly less contaminated with base than has previously been the case, especially where dimethylaniline has been employed. Our process has the further advantage that the basic contaminants which may be present in the antibiotic product are significantly less toxic than has previously been the case, and so the incidence of side effects on administration of the antibiotic may be reduced, if not substantially eliminated.

According to one embodiment of the invention, therefore, there is provided a process for the manufacture of a 6-acylaminopenicillanic acid antibiotic product by acylating a mono- or bis- silylated derivative of 6-aminopenicillanic acid with an acid chloride or protected acid chloride corresponding to the desired 6-acylamino group in an inert organic solvent in the presence of a hydrogen halide acceptor, cleaving silyl groups and any other protecting groups in the resultant product and recovering the desired penicillin antibiotic, wherein the hydrogen halide acceptor is a compound of formula (I)

$$R^1CONHR^2 \quad\quad (I)$$

wherein $R^1$ is a $C_{1-6}$ alkyl or aralkyl group or an amino group substituted by one or two $C_{1-6}$ alkyl groups and $R^2$ is a hydrogen atom or a $C_{1-6}$ alkyl or aralkyl group.

The mono- or bis-silylated derivative of 6-APA may have the formula (II)

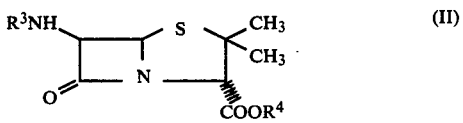

wherein $R^3$ represents a hydrogen atom or a silyl group $-SiR^5R^6R^7$ and $R^4$ represents a silyl group $-SiR^5R^6R^7$, the groups $R^5$, $R^6$ and $R^7$ being the same or different in each case and being selected from alkyl (e.g. $C_{1-6}$), aryl (e.g. $C_{5-12}$) and aralkyl (e.g. $C_{7-20}$) groups.

The acid chloride employed in the acylation is chosen according to the nature of the desired 6-acylamino group. When the latter contains sensitive groups it may be necessary to protect these during the process of the invention. Thus, in manufacturing ampicillin for example, the $\alpha$-amino group of the D(−)-$\alpha$-phenylglycyl chloride may conveniently be protected as its hydrochloride. The process according to the invention is generally applicable to the manufacture of known semi-synthetic penicillin antibiotics, for example, ampicillin, cloxacillin and dicloxacillin, the nature of which is well defined in existing literature.

Preferred compounds of formula (I) for use in the reaction include those wherein $R^1$ represents a $C_{1-4}$ alkyl group e.g. a methyl, ethyl, propyl or butyl group, for example N-methylacetamide. It is also preferred, however, that $R^2$ represents a hydrogen atom. The compound wherein $R^1$ represents a methyl group and $R^2$ represents a hydrogen atom i.e., acetamide, is particularly preferred because it is non-toxic.

The compound of formula (I) is desirably present in a quantity of from 1.0 to 4.0 times the stoichiometric amount of 6-APA, i.e., from 1-4 moles of compound per mole of 6-APA. The preferred amount is from 1.5-2.5 times and most preferably approximately twice the stoichiometric amount.

The compound of formula (I) is desirably added in the appropriate amount to the solution in which the mono- or bis-silylated derivative of the 6-APA has been prepared. Where a silylating agent is used which on reaction generates a base of formula (I), the quantity of base added for the acylation reaction may be appropriately reduced. The solution may be cooled to from $+10°$ to $-30°$ C., for example $+5°$ to $-25°$ C., e.g. from $+5°$ to $-5°$ C., prior to addition of the compound of formula (I) and once the compound has been added, the acylating agent may be added. The acylating agent may also be added before the addition of the compound of formula (I). The acylating agent may be added in one step or over a period of time.

The inert solvent in which the acylation reaction is effected may be, for example, a halogenated hydrocarbon or an aromatic hydrocarbon for example methylene chloride, ethylene chloride, chloroform, benzene or toluene. Methylene chloride is preferred.

Temperature control is desirably maintained throughout the acylation reaction, which proceeds comparatively rapidly and will generally be complete within from 30 minutes to 3 hours, for example about one and a half hours. The extent of the acylation may be monitored by, for example, determining the proportion or residual starting material by thin-layer chromatography. We generally prefer in the acylation step to employ a stoichiometric amount of the acyl chloride e.g. up to 1 equivalent, advantageously 1.0 equivalent, relative to the quantity of silylated 6-APA.

After completion of the acylation reaction, for example as evidenced by consumption of all the starting material, the resulting mixture or suspension may be cooled and treated with a compound containing active hydrogen, e.g. water, acidified or basified water, an alcohol or a phenol, to remove any silyl groups present in the penicillin reaction product. Water is the preferred desilylating agent for this purpose. Insoluble materials present in the reaction mixture, e.g. insoluble salts derived from a hydrogen chloride binder employed during silylation, may also conveniently be separated before desilylation, for example by filtration or centrifugation.

The penicillin antibiotic may then be precipitated, e.g. in the case of ampicillin, by adjusting the pH of the diluted reaction solution to the isoelectric point with a base, or in the case of cloxacillin and dicloxacillin by formation of a salt thereof in an organic solvent, and the precipitate may be recovered and dried by conventional means. Where it is desired to form a salt of the penicillin antibiotic, this may be achieved by addition of a suitable base, for example an alkali metal alkanoate, e.g. sodium 2-ethyl hexanoate.

A wide range of silylated derivatives of formula (II) may be used in the acylation step and these may be prepared from 6-APA by any convenient method of silylation. Advantageously the silylating agent is a halosilane or a silazane, e.g. a compound having one of the formulae $R^5R^6R^7SiX$; $R^5R^6R^7Si.NR^5R^6$; $R^5R^6R^7Si.NH\ SiR^5R^6R^7$; $R^5R^6R^7Si.NH.COR$; $R^5R^6R^7Si.NH.CO.NH.SiR^5R^6R^7$; $R^5R^6R^7Si.NH.CO.NR.SiR^5R^6R^7$ or $RC(OSiR^5R^6R^7):NSiR^5R^6R^7$ where X is a halogen atom, e.g. a chlorine atom, and the various groups R, $R^5$, $R^6$ and $R^7$, which may be the same or different, represent alkyl (e.g. $C_{1-6}$) for example, methyl, ethyl, n-propyl, or isopropyl; aryl, (e.g. $C_{5-12}$), for example phenyl; or aralkyl, (e.g. $C_{7-20}$), for example benzyl, groups. Preferred groups for R, $R^5$, $R^6$ and $R^7$ are methyl and phenyl, as in, for example, hexamethyldisilazane [$(Me_3Si)_2$ NH]. It will be appreciated that mixtures of silylating agents may be used to silylate the 6-APA e.g. hexamethyldisilazane and trimethylchlorosilane.

Examples of suitable silylating agents are trimethyl chlorosilane, hexamethyldisilazane, triethyl chlorosilane, triethyl bromosilane, tri-n-propyl chlorosilane, bromomethyl dimethyl chlorosilane, tri-n-butyl chlorosilane, methyl diethyl chlorosilane, dimethyl ethyl chlorosilane, phenyl dimethyl bromosilane, benzyl methyl ethyl chlorosilane, phenyl ethyl methyl chlorosilane, triphenyl chlorosilane, tri-o-tolyl chlorosilane, tri-p-dimethylaminophenyl chlorosilane, N-ethyl triethylsilylamine, hexaethyldisilazane, triphenyl silylamine, tri-n-propyl silylamine, tetraethyl dimethyl disilazane, tetramethyl diethyl disilazane, tetramethyl diphenyl disilazane, hexaphenyldisilazane, hexa-p-tolyl disilazane, N,O-bis-trimethylsilyacetamide, N-trimethylsilylacetamide, N-(triphenylsilyl)ethylcarbamate, N-(triethylsilyl)urea, N,N'-bis(trimethylsilyl)urea, and N-methyl-N-trimethylsilyl acetamide.

Where a silyl halide is employed as the silylating agent, the silylation will generally be conducted in an inert organic solvent. Halogenated hydrocarbons and aromatic hydrocarbons are very suitable. Examples of such solvents include benzene, toluene, methylene chloride, ethylene chloride or chloroform. The silylation is effected in the presence of a nitrogen base such as, for example, triethylamine, dimethylamine or trimethylamine, the base serving as a hydrogen halide acceptor; the amount of nitrogen base employed is preferably substantially equivalent to the quantity of silyl halide used. Where a silazane is employed as the silylating agent, the silylation is conveniently effected by heating the silazane and 6-APA with or without an inert solvent so that ammonia or amine derivatives formed as by products of the reaction are distilled off. Where a silylamide or a silyl urea is employed as a silylating agent, the silylation may be effected simply by heating the 6-APA and the silylating agent in an inert organic solvent until dissolution of the 6-APA occurs. Thereafter the resulting silylated derivative may, if desired, be isolated, for example by evaporation of the solvent.

According to a preferred embodiment of the process of this invention, a suspension of 6-APA is mono- or bis-silylated by reaction with a silylating agent and the resulting silylated 6-APA derivative is acylated directly in the same solution, without any intermediate separation. Silylation and acylation in accordance with this embodiment renders the overall process particularly simple and convenient since, for example, avoidance of the need to change the solvent after silylation significantly reduces plant requirements and operational costs. Thus in such a process it is simply necessary after silylation to adjust the temperature and to add the compound $R^1.CONHR^2$ (wherein $R^1$ and $R^2$ are as defined above) to the solution, adjust the temperature and add the acyl chloride. It is preferred to stir the reaction system during this last addition at least, and portionwise addition of the acyl chloride may be employed.

Where an excess of a strong base as triethylamine is employed as hydrogen halide binding agent in the silylation reaction it is possible to neutralise any residual strong base before acylation of the silylated 6-APA derivative, since such residual strong base might otherwise be detrimental. Any residual strong base may be neutralised by adding a mineral acid salt of a weak base (e.g. having a pKa not exceeding 7.0) to the reaction system before addition of any acyl chloride, for example acetamide hydrochloride.

The process according to the invention is particularly applicable to the manufacture of ampicillin, 6-(D-2-amino-2-phenylacetamido)-2,2-dimethylpenam-3-carboxylic acid, either as a hydrate e.g. the trihydrate or in an anhydrous form, or as a salt. Other semisynthetic penicillin antibiotics which may be manufactured by the process of this invention include amoxycillin, cloxacillin, dicloxacillin, α-carboxybenzylpenicillin esters, oxacillin, fluorcloxacillin and metacillin.

The invention will now be more particularly described in the following Examples which should not be construed as limiting the invention.

In the Examples, the nature and purity of the end products were determined by standard techniques, including polarimetry, spectrophotometry, iodometry, acidimetry and bioassay.

A description of the spectrophotometric method used to assay the ampicillin may be found in British Pharmacopoeia, (1973, H.M.S.O) on p. 30; a description of the iodometric method used is given in "Cephalosporins and Penicillins—Chemistry and Biology" Ed. Flynn (Academic Press, 1972) on pp. 613–614; a description of the bioassay technique used is given in British Pharmacopoeia (1973, H.M.S.O) on pp. 102–104 of the Appendix; and an account of the acidimetric assay used to assay the cloxacillin and dicloxacillin is given in British Pharmacopoeia (1973, H.M.S.O.) on page 81. The water content was determined by a Karl Fischer analysis for cloxacillin and dicloxacillin, and by the same method or by measuring the weight loss on heating to form the anhydrous compound in the case of ampicillin trihydrate.

The purity of the ampicillin products is given after allowance has been made for the water (hydrate) content of the ampicillin product obtained.

In the Examples, the specific rotation of ampicillin trihydrate is determined at c=0.25% solutions in water, and the specific rotations of dicloxacillin and cloxacillin are determined at c=1.0% in water, the determinations being carried out at 20° C.

The specific rotation of anhydrous ampicillin is given as $[\alpha]_D^{20} = +280°$ to $+300°$ (c=0.25 in water) and that of cloxacillin as sodium salt monohydrate is given as $[\alpha]_D^{20} = +156°$ to $+164°$ (c=1 in water) in the British Pharmacopoeia (1973, H.M.S.O). That of dicloxacillin as sodium salt monohydrate is given as $[\alpha]_D^{24} = +134°$ (c=0.4 in water) in the Merck Index (8th Edition).

EXAMPLE 1

Preparation of 6-(D-2-amino-2-phenylacetamido)-2,2-dimethylpenam-3-carboxylic acid using acetamide as base 52.9 ml (0.380 mols) of triethylamine were added under stirring to a suspension of 43.2 g (0.200 mols) of 6-aminopenicillanic acid in 350 ml of methylene chloride. The temperature of the suspension was adjusted to +15° C. and addition was made over five minutes of 53.0 ml (0.420 mols) of trimethylchlorosilane; on completion of the addition, the temperature was found to be between +35° C. and +40° C. Stirring was continued for another 60 minutes at +40° C. The suspension was cooled to −25° C., and 23.6 g (0.400 mols) of acetamide and thereafter 43.3 g (0.200 mols; purity 95.0%) of D(−)-α-phenylglycylchloride hydrochloride were added. The temperature was allowed to increase to −5° C. and held at this temperature for a total time of 90 minutes starting from the addition of the acid chloride hydrochloride. 450 ml of water were added. Ampicillin trihydrate was precipitated by adjusting the pH to 4.5 with dilute NH₄OH. After stirring for 60 minutes at +10° C./+15° C. the product was filtered and then washed with 2×75 ml of water and 3×125 ml of acetone and then dried at +35° C./+40° C. to yield a white crystalline odourless powder. Yield: 83.5%±1%

Specific rotation: +296°±1°, (obtained from a value of +256°±1° for the hydrated compound)

Iodometric assay: 98.6%±0.5% purity (obtained from an ampicillin purity of 85.4±0.5% for the hydrated compound)

Spectrophotometric assay: 98.5%±0.5% (obtained from an ampicillin purity of 85.3±0.5% for the hydrated compound)

Bioassay: 98.8±1.0% purity (obtained from a purity of 85.6±1.0% for the hydrated compound)

Water content: 13.4%.

EXAMPLE 2

Preparation of 6-(D-2-amino-2-phenylacetamido)-2,2-dimethylpenam-3-carboxylic acid trihydrate using acetamide as base 48.9 ml (0.200 mols) of N,O-bis-trimethylsilylacetamide were added to a suspension of 43.2 g (0.200 mols) of 6-aminopenicillanic acid in 350 ml of methylene chloride with agitation. The mixture was heated at +40° C. for 120 minutes and then cooled to −25° C., and 11.8 g (0.200 mols) of acetamide were added. Thereafter the procedure followed was as described in Example 1 to yield ampicillin trihydrate in 80.8% yield.

Specific rotation: +298°.
Spectrophotometric assay: 99.1%
Water content: 13.9%.

EXAMPLE 3

Preparation of 6-(D-2-amino-2-phenylacetamido)-2,2-dimethylpenam-3-carboxylic acid trihydrate using N-methylacetamide as base 52.9 ml (0.380 mols) of triethylamine were added to a suspension of 43.2 g (0.200 mols) of 6-aminopenicillanic acid in 350 ml of methylene chloride under agitation. The temperature of the suspension was adjusted to +15° C. and, over a period of 5 minutes, 53.0 ml (0.420 mols) of trimethylchlorosilane were added. After the addition, the temperature was between +35° C. and +40° C. Agitation was continued for a further 60 minutes at +40° C. The suspension was cooled to −25° C., addition was made of 36.6 g (0.500 mols) of N-methylacetamide, and the procedure followed thereafter was as that described in Example 1. A yield of 84.4% was obtained.

Specific rotation: +295°
Spectrophotometric assay: 98.6%

Water content: 14.0%.

EXAMPLE 4

Preparation of 6-(D-2-amino-2-phenylacetamido)-2,2-dimethylpenam-3-carboxylic acid trihydrate using N-ethyl-acetamide as base 52.9 ml (0.380 mols) of triethylamine were added to a suspension of 43.2 g (0.200 mols) of 6-aminopencillanic acid in 350 ml of methylene chloride under agitation. The temperature of the suspension was adjusted to +15° C. and 53.0 ml (0.420 mols) of trimethylchlorosilane were added over 5 minutes. At the end of the addition, the temperature of the mixture was between +35° C. and +40° C. The agitation was maintained for a further 60 minutes at +40° C. The suspension was cooled to −5° C., and 34.8 g (0.400 mols) of N-ethyl-acetamide were added, and the procedure followed thereafter was as that described in Example 1 except that the acid chloride hydrochloride was added at −5° C. and reaction temperature was 0° C. for 90 minutes.
Yield: 74.7%.
Spectrophotometric assay: 96.4%
Specific rotation: +293°
Water content: 13.4%.

EXAMPLE 5

Preparation of 6-[3-(2,6-dichlorophenyl)-5-methyl-4-isoxazolecarboxamido]-2,2-dimethylpenam-3-carboxylate (Dicloxacillin) sodium monohydrate using acetamide as base 52.9 ml (0.380 mols) of triethylamine were added to a suspension of 43.2 g (0.200 mols) of 6-aminopenicillanic acid in 350 ml of methylene chloride under agitation. The temperature of the suspension was adjusted to +15° C. and, over 5 minutes, 53.0 ml (0.420 mols) of trimethylchlorosilane were added. At the end of the addition the temperature was between +35° C. and +40° C. The agitation was maintained for a further 60 minutes at +40° C. The suspension was cooled to −25° C., and 23.6 g (0.400 mols) of acetamide and then 58.1 g (0.200 mols) of 3-(2,6-dichlorophenyl)-5-methylisoxazolyl-4-carbonylchloride were added. The temperature was allowed to increase to 0° C. and was held there for a total time of 60 minutes starting from the addition of the acid chloride. 175 ml of methyl isobutyl ketone and 300 ml of water were then added; the phases were separated and the aqueous phase was discarded; the organic phase was again washed with 300 ml of water, and the aqueous phase was discarded. The organic phase was treated for 30 minutes with anhydrous sodium sulphate; the drying agent was then filtered, and washed with 175 ml of methylisobutylketone, which, after separation, was combined with the main organic phase. The sodium salt monohydrate of dicloxacillin was then precipitated by adding to the combined organic phases 200 ml of a 1 N solution of sodium 2-ethyl-hexanoate in methylisobutylketone. After 60 minutes agitation the crystalline white solid was filtered, and then washed with 3×150 ml of acetone; drying was in vacuum oven at +35° C./+40° C.
Yield: 87.2%.
Acidimetric assay: 98.6% as sodium salt monohydrate.
Specific rotation: +139°
Water content: 3.8%.

EXAMPLE 6

Preparation of 6-[3-(2-chlorophenyl)-5-methyl-4-isoxazolecarboxamido]-2,2-dimethylpenam-3-carboxylate (cloxacillin) sodium monohydrate using acetamide as base 52.9 ml (0.380 mols) of triethylamine were added to a suspension of 43.2 g (0.200 mols) of 6-aminopenicillanic acid in 350 ml of methylene chloride under agitation. The temperature of the suspension was adjusted to +15° C. and over 5 minutes, 53.0 ml (0.420 mols) of trimethylchlorosilane were added. At the end of the addition the temperature was between +35° C. and +40° C. Agitation was continued for another 60 minutes at +40° C. The suspension was cooled to −25° C., 23.6 g (0.400 mols) of acetamide and then 51.2 g (0.200 mols) of 3-(2-chlorophenyl)-5-methylisoxazolyl-4-carbonyl chloride) were added. The temperature was allowed to increase to 0° C. and was held there for a total period of 60 minutes starting from the addition of the acid chloride. 175 ml of methyl isobutyl ketone and 300 ml of water were then added, the phases separated, and the aqueous phase discarded. The organic phase was again washed with 300 ml of water, and the aqueous phase was discarded. The organic phase was dried for 30 minutes with anhydrous sodium sulphate. The latter was then filtered off and washed with 175 ml of methyl isobutyl ketone, which, after separation, was combined with the main organic phase. The sodium cloxacillin monohydrate was then precipitated by adding to the combined organic phases 200 ml of a 1 N solution of sodium 2-ethyl-hexanoate in methyl isobutyl ketone. After 60 minutes agitation the crystalline white solid was filtered washed with 3×150 ml of acetone and dried in a vacuum oven at +35° C./+40° C.
Yield: 86.2%
Acidimetric assay: 98.8% as sodium salt monohydrate
Specific rotation: +163°
Water content: 3.9%

EXAMPLE 7

Preparation of 6-[3-(2,6-dichlorophenyl)-5-methyl-4-isoxazolecarboxamido]-2,2-dimethylpenam-3-carboxylic acid (Dicloxacillin) using acetamide as base 53 ml (0.42 mols) Trimethylchlorosilane were slowly added over a period of 10 minutes at +10° C. to a mixture of 43.2 g (0.20 mols) of 6-aminopenicillanic acid, 350 ml of methylene chloride and 53 ml (0.38 mols) triethylamine. The mixture was heated at about 35°/40° C. for an hour and then cooled to −5° C., when 23.6 g (0.40 mols) acetamide were added. After 15 minutes, the mixture was cooled to −25° C. and 58.0 g (0.20 mols) of 3-(2,6-dichlorophenyl)-5-methylisoxazolyl-4-carbonyl chloride were added, the temperature being maintained below −10° C. After stirring for one hour at 0° C., 250 ml water were added, the mixture was separated and washed again with 250 ml water. The organic layer was treated with a drying agent and dicloxacillin was recovered as the sodium salt monohydrate by adding a stoichiometric amount of sodium 2-ethylhexanoate.
Yield: 80.6%
Acidimetric assay: 96% as sodium salt monohydrate
Specific rotation: +134°

EXAMPLE 8

Preparation of 6-(D-2-amino-2-phenylacetamido)-2,2-dimethylpenam-3-carboxylic acid trihydrate using acetamide as base 53 ml (0.42 mols) of trimethylchlorosilane were slowly added, during a period of 10 minutes at +10° C. to a mixture of 43.2 g (0.20 mols) of 6-aminopenicillanic acid, 350 ml of methylene chloride and 53 ml (0.38 mols) of triethylamine. The mixture was heated at about +35°/40° C. for 1 hour, and then cooled to −5° C. when 23.6 g (0.40 mols) of acetamide were added. After 15 minutes, 43.2 g (purity: 95%; 0.20 mols) of D-(−)-α-phenylglycylchloride hydrochloride were added, maintaining the temperature below 0° C. After stirring for 1.5 hours, between 0° C. and +10° C., the temperature was lowered to 0° C. and 450 ml of water were added. Ampicillin trihydrate was precipitated by adjusting the pH to 4.5 with diluted $NH_4OH$; the crystalline product was filtered, washed with water and acetone, and then dried.
Yield: 80.3%
Spectrophotometric assay: 98.9%
Specific rotation: +293°
Water content: 13.4%

EXAMPLE 9

Preparation of 6-(D-2-amino-2-phenylacetamido)-2,2-dimethylpenam-3-carboxylic acid trihydrate using acetamide as base A mixture of 43.2 g (0.20 mols) of 6-aminopenicillanic acid, 350 ml of methylene chloride and 25.0 g (0.155 moles) of hexamethyldisilazane was heated under reflux for 4 hours. The turbid mixture was cooled to −5° C., whereupon 23.6 g (0.40 mols) acetamide were added. The procedure of Example 10 was then followed to obtain ampicillin trihydrate.
Yield: 77.2%
Spectrophotometric assay: 98.3%
Specific rotation: +292°
Water content: 13.5%

EXAMPLE 10

Preparation of 6-(D-2-amino-2-phenylacetamido)-2,2-dimethylpenam-3-carboxylic acid trihydrate using acetamide as base The procedure of Example 10 was followed except that chloroform was used as solvent in place of methylene chloride.
Yield: 76.0%
Spectrophotometric assay: 98.0%
Specific rotation: +291°
Water content: 13.2%

EXAMPLE 11

Preparation of 6-(D-2-amino-2-phenylacetamido)-2,2-dimethylpenam-3-carboxylic acid trihydrate using N-methylurea as base The process of Example 1 was repeated except that 22.2 g (0.300 moles) of N-methylurea were used instead of acetamide.
A yield of 81.9% was obtained,
Specific rotation: 296°
Spectrophotometric assay: 98.7%
Water content: 13.4%

EXAMPLE 12

Preparation of 6-(D-2-amino-2-phenylacetamido)-2,2-dimethylpenam-3-carboxylic acid trihydrate using 1,3-dimethylurea as base The process of Example 1 was followed except that 52.9 g (0.600 moles) of 1,3-dimethylurea were used instead of acetamide.
A yield of 84.1% was obtained
Specific rotation: 296°
Spectrophotometric assay: 98.3%
Water content: 13.4%

EXAMPLE 13

Preparation of 6-(D-2-amino-2-phenylacetamido)-2,2-dimethylpenam-3-carboxylic acid trihydrate using 1,1-dimethylurea as base.

The process of Example 1 was followed except that 35.2 g (0.40 moles) of 1,1-dimethylurea were used instead of acetamide and once silylation had been effected, the temperature was lowered to only −5° C. and the acid chloride hydrochloride was added at −5° C. instead of −25° C. Acylation was effected at 0° C. for 90 minutes.
A yield of 80.2% was obtained.
Specific rotaion: 291°
Spectrophotometric assay: 97.3%
Water content: 13.4%

EXAMPLE 14

Preparation of 6-(D-2-amino-2-phenylacetamido)-2,2-dimethylpenam-3-carboxylic acid trihydrate using acetamide as base.

The process of Example 1 was followed except that freshly recrystallised 6-aminopenicillanic acid (purity 98.1%) was used.
A yield of 86.2% was obtained
Specific rotation: 296°
Spectrophotometric assay: 98.3%
Water content: 13.3%

EXAMPLE 15

Preparation of 6-(D-2-amino-2-phenylacetamido)-2,2-dimethylpenam-3-carboxylic acid trihydrate using acetamide as base The process of Example 1 was followed except that 6-aminopenicillanic acid obtained by enzymic cleavage of penicillin G and of purity 99.4% was used.
Specific rotation: 295°
Spectrophotometric assay: 98.3%
Water content: 13.3%

We claim:
1. In a process for the manufacture of a 6-acylaminopenicillanic acid antibiotic product by acylating a mono- or bis-silylated derivative of 6-aminopenicillanic acid with an acid chloride or protected acid chloride corresponding to the desired 6-acylamido group at a temperature from about +10° to about −30° C. in an inert organic solvent in the presence of from about 1.0 to about 4.0 times the stoichiometric amount of a hydrogen halide acceptor, cleaving silyl groups with water and other protecting groups in the resultant product and recovering the desired antibiotic product, the improvement which comprises em- ploying a hydrogen halide acceptor which is a compound of formula (I)

$$R^1CONHR^2 \quad (I)$$

wherein $R^1$ is selected from the group consisting of $C_{1-6}$ alkyl, $C_{7-20}$ aralkyl and amino substituted by one or two $C_{1-6}$ alkyl groups and $R^2$ is selected from the group consisting of hydrogen, $C_{1-6}$ alkyl and $C_{7-20}$ aralkyl.

2. The process of claim 1 wherein $R^1$ represents a $C_{1-4}$ alkyl group and $R^2$ represents a hydrogen atom.

3. The process of claim 1 wherein the compound of formula (I) is acetamide.

4. The process of claim 1 wherein the compound of formula (I) is N-methylacetamide.

5. The process of claim 3 wherein the compound of formul (I) is used in an amount approximately twice the stoichiometric amount of 6-aminopenicillanic acid.

6. The process of claim 1 wherein the protected acid chloride is D(−)-α-phenylglycyl chloride hydrochloride.

7. The process of claim 1 wherein the acid chloride is 3-(2,6-dichlorophenyl)-5-methylisoxazolyl-4-carbonyl chloride.

8. The process of claim 1 wherein the acid chloride is 3-(2-chlorophenyl)-5-methylisoxazolyl-4-carbonyl chloride.

9. In a process for the manufacture of ampicillin or a salt or hydrate thereof by acylating a mono- or bis-silylated derivative of 6-aminopenicillanic acid with D-(−)-phenylglycyl chloride hydrochloride at a temperature from about +10° to about −30° C. in methylene chloride in the presence of from about 1.5 to about 2.5 times the stoichiometric amount of hydrogen halide acceptor, cleaving silyl groups with water and other protecting groups in the resultant product and recovering the desired ampicillin product, the improvement which comprises employing acetamide as hydrogen halide acceptor.

10. The process of claim 9 wherein ampicillin trihydrate is recovered.

* * * * *